(12) United States Patent
Bailey et al.

(10) Patent No.: US 10,736,992 B2
(45) Date of Patent: Aug. 11, 2020

(54) BIOMOLECULAR PATTERNING OF THREE DIMENSIONAL TISSUE SCAFFOLDS

(75) Inventors: Ryan C. Bailey, Urbana, IL (US);
Brendan A. Harley, Urbana, IL (US);
Teresa A. Martin, Champaign, IL (US);
Steven R. Caliari, Urbana, IL (US)

(73) Assignee: BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 2117 days.

(21) Appl. No.: 14/001,327

(22) PCT Filed: Feb. 27, 2012

(86) PCT No.: PCT/US2012/026761
§ 371 (c)(1),
(2), (4) Date: Aug. 29, 2013

(87) PCT Pub. No.: WO2012/116363
PCT Pub. Date: Aug. 30, 2012

(65) Prior Publication Data
US 2019/0192735 A1    Jun. 27, 2019

Related U.S. Application Data

(60) Provisional application No. 61/446,794, filed on Feb. 25, 2011.

(51) Int. Cl.
*A61L 27/38* (2006.01)
*A61K 35/12* (2015.01)
*A61L 27/50* (2006.01)
*A61L 27/56* (2006.01)
*A61K 35/32* (2015.01)
*A61L 27/54* (2006.01)
*A61L 27/26* (2006.01)
*A61L 27/48* (2006.01)
*C08B 37/00* (2006.01)
*C12N 5/00* (2006.01)
*C12N 5/077* (2010.01)
*A61K 38/18* (2006.01)
*A61K 38/30* (2006.01)

(52) U.S. Cl.
CPC .............. *A61L 27/38* (2013.01); *A61K 35/12* (2013.01); *A61K 35/32* (2013.01); *A61L 27/26* (2013.01); *A61L 27/48* (2013.01); *A61L 27/50* (2013.01); *A61L 27/54* (2013.01); *A61L 27/56* (2013.01); *C08B 37/0063* (2013.01); *C12N 5/0062* (2013.01); *C12N 5/0654* (2013.01); *C12N 5/0655* (2013.01); *C12N 5/0657* (2013.01); *C12N 5/0658* (2013.01); *A61K 38/1858* (2013.01); *A61K 38/30* (2013.01); *A61L 2430/02* (2013.01); *A61L 2430/06* (2013.01); *A61L 2430/20* (2013.01); *A61L 2430/28* (2013.01); *A61L 2430/30* (2013.01); *A61L 2430/32* (2013.01); *A61L 2430/40* (2013.01); *C12N 2533/54* (2013.01)

(58) Field of Classification Search
None
See application file for complete search history.

(56) References Cited

U.S. PATENT DOCUMENTS

| 5,288,514 A * | 2/1994 | Ellman | A61K 49/0004 |
| | | | 427/2.13 |
| 7,579,189 B2 * | 8/2009 | Freyman | A61L 27/3604 |
| | | | 424/400 |
| 2005/0169962 A1 | 8/2005 | Bhatia | |
| 2008/0260798 A1 | 10/2008 | Freyman | |
| 2011/0015739 A1 | 1/2011 | Cheung | |

FOREIGN PATENT DOCUMENTS

WO       2010/030964      3/2010

OTHER PUBLICATIONS

Toh, C. et al., Langmuir 2009, vol. 25, pp. 8894-8898.*
International Search Report for corresponding PCT Application No. PCT/US2012/026761, dated Jun. 7, 2012.
Kuo et al., Mechanoactive Tenogenic Differentiation of Human Mesenchymal Stem Cells, Tissue Engineering, 14 (2008) (10):1615-1627.
Fink et al., "Comparative study and improvement of current cell micro-patterning techniques", Lab Chip, 7:672-680 (2007).
Harley and Gibson, "In vivo and in vitro applications of collagen-GAG scaffolds", Chemical Engineering Journal, (2008) 137:102-121.
O'Brien et al., "Influence of freezing rate on pore structure in freeze-dried collagen-GAG scaffolds", Biomaterials, (2004) 25:1077-1086.
Tierney et al., "Oseteoblast activity on collagen-GAG scaffolds is affected by collagen and GAG concentrations", J. Biomed Mater Res A. 91:92-101 (2009).
Toh et al., "Direct Biophotolithographic Method for Generating Substrates with Multiple Overlapping Biomolecular Patterns and Gradients", Langmuir Letter, 25(16):8894-8898 (2009).

(Continued)

Primary Examiner — Heidi Reese
(74) Attorney, Agent, or Firm — DLA Piper LLP (57) ABSTRACT

The invention provides methods and compositions for making and using collagen-glycosaminoglycan three-dimensional scaffolds immobilized with biomolecules that are spatially and temporally patterned. The method comprises adding benzophenone to a collagen-glycosaminoglycan three dimensional scaffold in the dark; adding one or more biomolecules to one or more areas of the collagen-glycosaminoglycan three-dimensional scaffold (which can be done optionally in the dark or in the light); and exposing the collagen-2glycosaminoglycan three-dimensional scaffold to light at a wavelength of about 350 to about 365 nm.

11 Claims, 4 Drawing Sheets

(56) References Cited

OTHER PUBLICATIONS

Chan and Yousaf, "A photo-electroactive surface strategy for immobilizing ligands in patterns and gradients for studies of cell polarization", Molecular Biosystems, 4:746-753 (2008).

Davidenko et al., "Collagen-hyaluronic acid scaffolds for adipose tissue engineering", Acta Biomaterialia, 6:3957-3968 (2010).

Davidson, "The Photoreduction of Benzophenone by Amines", Chemical Communications, 16:575 (1966).

Gulotta et al., "Stem Cells Genetically Modified with the Developmental Gene MT1-MMP Improve Regeneration of the Surpraspinatus Tendon-to-Bone Insertion Site", The American Journal of Sports Medicine, 38(7):1429 (2009).

Harley et al., "Design of a multiphase osteochondral scaffold III: Fabrication of layered scaffolds with continuous interfaces", J. Biomed Mater Res A. 92:1078-1093 (2010).

Kim et al., "Fluorometric Assay of DNA in Cartilage Explants using Hoechst 33258", Analytical Biochemistry, 174:168-176 (1988).

Liu et al., "Targeted delivery system for juxtacrine signaling growth factor based on rhBMP-2-mediated carrier-protein conjugation", Bone 39:825-836 (2006).

Murphy et al., "The effect of mean pore size on cell attachment, proliferation and migration in collagen-glycosaminoglycan scaffolds for bone tissue engineering", Biomaterials, 31:461-466 (2010).

O'Brien et al., "The effect of pore size on cell adhesion in collagen-GAG scaffolds", Biomaterials, 26:433-441 (2005).

Parikka et al., "Human mesenchymal stem cell derived osteoblasts degrade organic bone matrix in vitro by matrix metalloproteinases", Matrix Biology, 24:438-447 (2005).

Sethi et al., "Evidence for sequential utilization of fibronectin, vitronectin, and collagen during fibroblast-mediated collagen contraction", Wound Repair Regen., 10:397-408 (2002).

Sinsheimer et al., "Polycyclic Aromatic Isothiocyanate Compounds as Fluorescent Labeling Reagents", J. Pharm Sci., 64:925-930 (1975).

\* cited by examiner

BP Conjugation to Scaffolds:

BP reacts with free
lysine side chains

Photoimmobilization of Biomolecules:

Soak in biomolecule
solution, irradiate at 365 nm

Figure 4 ature-of about 350 to about 365 nm. One or more portions of the collagen-glycosaminoglycan three-dimensional scaffold can be exposed to the light while one or more other portions of the scaffold can remain in the dark. The one or more types of biomolecules can be immobilized onto the scaffold at two or more different depths into the scaffold. The two or more types of biomolecules can be immobilized to the scaffold and can be immobilized to two or more areas of the scaffold, or to two or more depths in the scaffold, or both. A first mask can be placed over the collagen-glycosaminoglycan three-dimensional scaffold prior to exposing the collagen-glycosaminoglycan three-dimensional scaffold to the light.

BIOMOLECULAR PATTERNING OF THREE DIMENSIONAL TISSUE SCAFFOLDS

PRIORITY

This application claims the benefit of U.S. Ser. No. 61/446,794, filed Feb. 25, 2011, which is incorporated herein by reference in its entirety.

GOVERNMENT INTEREST

This invention was made with government support under contract number NIH NIGMS T32GM070421, DE-FG02-07ER46453, and DE-FG02-07ER46471 awarded by the United States National Institutes of Health and the United States Department of Energy. The United States government has certain rights in the invention.

BACKGROUND OF THE INVENTION

The extracellular matrix (ECM) is a complex organization of structural proteins such as collagens and proteoglycans. A wide variety of tissue engineering scaffolds have been created in attempts to mimic features of the native ECM. Notably, microstructural features [1-3], mechanical properties [4-6], and inclusion of soluble or insoluble biomolecules [7, 8] have all been shown to significantly influence cell behaviors such as adhesion, growth, and differentiation as well as to affect material bioactivity for in vivo applications. Heterogeneous tissues with spatially and temporally modulated properties and their biomaterial mimics play an important role in organism physiology and regenerative medicine [9, 10]. An example of particular relevance is the graded interfacial region found between bone and tendon in the musculoskeletal system, which contains complex compositional, microstructural, and mechanical patterns; the gradient interface reduces formation of interfacial stress concentrations that can lead to interface failure while maintaining distinct tendon and osseous compartments [11, 12].

With the understanding that the microstructure, mechanics, and composition of the ECM is dynamic and often spatially patterned or heterogeneous over the length-scale of traditional biomaterials, there has recently been significant effort aimed at moving away from static, monolithic biomaterials towards instructive biomaterials that provide specialized cell behavioral cues in spatially and temporally defined manners [13, 14]. These materials hypothetically recapitulate aspects of the dynamic and spatially heterogeneous constellation of cues presented by the ECM.

The development of molecularly general approaches to spatially control the presentation of multiple biomolecules within porous scaffolds is an important goal for creating advanced biomaterials. Many adhesion ligands, growth factors, and other biomolecules are typically sequestered as opposed to freely soluble within the ECM [28]. Biomolecule immobilization has further shown benefits relative to bolus or even controlled delivery of soluble growth factors [7]; explanations include extended biomolecule half-life, elimination of diffusive dilution [7], and avoidance of cellular uptake that limits long-term bioactivity. While a number of methods have been developed for creating spatial patterns of surface-immobilized biomolecules on 2D surfaces [16, 29-31, 32], many of these approaches are not amenable to patterning within porous scaffolds where conformal contact and/or confinement of fluid flow cannot be readily achieved.

A current limitation in biomaterials science is the lack of universal methods for creating multicomponent, overlapping patterns or gradients of biomolecules within a biomaterial with spatial and temporal control over presented surface densities.

Simple, yet generic tethering chemistries that enable spatial localization of wide range of biomolecules as well as exogenously or endogenously cued release of biomolecules onto a 3D scaffold from clinically relevant biomaterials are needed in the art. Current techniques do not currently exist to effectively separate biomaterial fabrication and spatially-controlled patterning of biomolecules in a manner that is applicable to the wide range of biochemical moieties in the native ECM.

SUMMARY OF THE INVENTION

One embodiment of the invention provides a method of immobilizing one or more types of biomolecules onto a collagen-glycosaminoglycan three-dimensional scaffold. The method comprises adding benzophenone to a collagen-glycosaminoglycan three-dimensional scaffold in the dark; adding one or more biomolecules to one or more areas of the collagen-glycosaminoglycan three-dimensional scaffold (which can be done optionally in the dark or in the light); and exposing the collagen-glycosaminoglycan three-dimensional scaffold to light at a wavelength of about 350 to about 365 nm. One or more portions of the collagen-glycosaminoglycan three-dimensional scaffold can be exposed to the light while one or more other portions of the scaffold can remain in the dark. The one or more types of biomolecules can be immobilized onto the scaffold at two or more different depths into the scaffold. The two or more types of biomolecules can be immobilized to the scaffold and can be immobilized to two or more areas of the scaffold, or to two or more depths in the scaffold, or both. A first mask can be placed over the collagen-glycosaminoglycan three-dimensional scaffold prior to exposing the collagen-glycosaminoglycan three-dimensional scaffold to the light.

Where a first mask is used, the method can further comprise placing the collagen-glycosaminoglycan three-dimensional scaffold in the dark and removing the first mask from the collagen-glycosaminoglycan three-dimensional scaffold; adding one or more biomolecules to one or more areas the collagen-glycosaminoglycan three-dimensional scaffold (which can be done optionally in the dark or in the light); placing a second mask over the collagen-glycosaminoglycan three-dimensional scaffold in the dark; exposing the collagen-glycosaminoglycan three-dimensional scaffold to light at a wavelength of about 350 to about 365 nm; and optionally repeating these steps with additional masks and biomolecules.

The one or more of the biomolecules can be immobilized to the scaffold via a cleavable linker. The cleavable linker can be cleavable by an exogenous cue or an endogenous cue.

Another embodiment of the invention provides a collagen-glycosaminoglycan three-dimensional scaffold comprising one or more biomolecules covalently immobilized to the scaffold in a distinct pattern. Two or more types of biomolecules can be covalently immobilized to the scaffold, wherein in each type of biomolecule is present in a unique distinct pattern. The one or more of the biomolecules can be immobilized to the scaffold via a cleavable linker. The cleavable linker can be cleavable by an exogenous cue or an endogenous cue. The scaffold can be seeded with cells. The one or more biomolecules can be immobilized to one or more different depths into the scaffold.

Yet another embodiment of the invention provides a method for tissue regeneration in a subject having a disorder characterized by tissue damage or loss comprising implanting or grafting a scaffold of the invention in or on the subject to induce tissue regeneration. The disorder can be a bone disorder, a cardiac disorder, a liver disorder, a macular degeneration disorder, a nerve disorder, a tissue disorder, or a skin disorder. The tissue can be, e.g., bone, cardiac tissue, conjunctiva tissue, liver tissue, articular cartilage, cartilage, tendon tissue, tissue, nerve tissue, muscle tissue, or skin.

Therefore, the invention provides compositions and methods required for complex tissue engineering applications. Of critical importance is the development of tools to recapitulate the dynamic biomolecular environments encountered in vivo, particularly the density and spatio-temporal distribution of multiple biomolecule signals. The invention provides universal methods for creating multicomponent, overlapping patterns or gradients of biomolecules within a 3D scaffold biomaterial with spatial and temporal control over presented surface densities.

The methods of the invention provide for the separation of biomaterials in a manner that separates biomaterial fabrication and biomolecule functionalization and allows for greater independence for manipulating microstructural and compositional cues. Separating fabrication and patterning steps from cell addition reduces the potential for adverse (i.e. cytotoxic) effects on cell bioactivity due to the biomolecule patterning strategy, increases the generality of the method for multiple cell types, and can ease clinical translation and commercial scale-up.

BRIEF DESCRIPTION OF THE DRAWINGS

FIG. 4 shows Light activated release strategy for removing covalently immobilized biomolecules. The "catch and release" moiety is constructed from two commercial components that are coupled via solid phase synthesis: ahydrazino-modified glycine which links to aryl aldehydes pre-installed on the scaffold (A), and a nitrobenzyl modified propionic acid, which provides the light activation cleavage strategy. Although the benzophenone conjugation reaction and the nitrobenzyl cleavage both are activated by UV light, the faster rate (~200x) of the conjugation reaction (B) will allow for biomolecules to be attached to the scaffold with minimal cleavage. Subsequently, at a defined time period after cells have infiltrated the scaffold and followed the immobilized instructive cues, exposure to low intensity UV light will release the pendant ligand (C).

DETAILED DESCRIPTION OF THE INVENTION

As used herein, the singular forms "a," "an," and "the" include plural referents unless the context clearly dictates otherwise.

Three Dimensional Scaffolds

Collagen-glycosaminoglycan (CG) scaffolds are a class of regulatory compliant biomaterials whose collagen and glycosaminoglycan (GAG) constituents demonstrate low antigenicity and immunogenicity. Collagen based scaffolds are synthesized as graft copolymers of collagen and glycosaminoglycan and are similar to the extracellular matrix (ECM). Collagen in the scaffolds can be collagen types I-XXVIII or combinations thereof. In one embodiment of the invention, collagen type I or type II is used. Glycosaminoglycan is a polysaccharide containing an amino sugar and uronic acid or galactose. Glycosaminoglycans in the scaffolds can include, for example, hyaluronic acid, chondroitin, chondroitin sulfate, chondroitin 6-sulfphate, dermatan sulfate, keratan sulfate, heparin, heparan sulfate, or combinations thereof.

Methods of generating three-dimensional CG scaffolds are known in the art. [1, 25, 26, 33, 34]. For example, CG scaffolds can be fabricated by freeze drying where an aqueous CG suspension is frozen, resulting in an interpenetrating network of ice crystals surrounding by CG content; sublimation removes the ice content, leaving behind an open-cell structure whose pores are defined by the ice crystals formed during freezing. Scaffold microstructure can be altered by controlling the directionality and kinetics of heat transfer. Their high porosity (>95%) allows rapid cell invasion and metabolite diffusion, making them ideal for acellular implantation; acellular strategies further reduce regulatory compliance requirements and speed clinical translation.

From a biomolecular patterning perspective, scaffolds offer advantages in terms of independent modulation of scaffold microstructural, mechanical, and compositional properties. Their open-cell nature also improves the speed of cell infiltration and metabolite diffusion compared to hydrogels, facilitating rapid clearance of biomolecules after release. Scaffold microstructure (porosity, mean pore size, pore shape, interconnectivity, and specific surface area) and mechanical properties (Young's modulus) have been shown to significantly influence cell behaviors such as adhesion, growth, and differentiation.

In contrast to conventional two-dimensional cell culture systems (flat 2D surfaces such as membranes, culture dishes, or multi-well tissue culture plates where cells grow in monolayers), three-dimensional scaffolds mimic the complex three-dimensional cellular structure of living tissues by providing an adhesive substrate for cells and by acting as a three-dimensional physical, porous support for cells in culture and in vivo. Methods and compositions of the invention provide for patterning of 3D GC scaffolds with biomolecules in three dimensions.

CG scaffolds can be altered for specific applications. For example, a CG scaffold can be mineralized for bone repair. In one embodiment of the invention calcium phosphate is added during the fabrication of the scaffold for a mineral: organic component ratio of about 0.01, 0.02, 0.03, 0.04, 0.05, 0.06, 0.07, 0.08, 0.09 or more. The chemical and pore structural compositions of these mineralized scaffolds mimic the properties found in bone tissue [21, 42]. A liquid-phase co-synthesis methodology allows for the construction of multi-phase scaffolds with a mineralized part and an organic (collagen-GC) part with no hard interfaces between the two parts. Id. These scaffolds are useful in, for example, the repair of joints.

Additionally, a multicompartment CG scaffold can be constructed for use in, e.g., osteochondral (cartilage-underlying bone) repair via, e.g., liquid phase cosynthesis interdiffusion of unmineralized, type II collagen-glycosaminoglycan and mineralized, type I collagen-glycosaminoglycan (CGCaP) suspensions followed by freeze drying to produce a porous, layered osteochondral scaffold with a soft interface. [18]. A CG bone-tendon-interface scaffold can be made with directional freeze drying to create scaffolds with differing levels of anisotropy and an evaporative process to create high-density CG scaffolds.

By modifying freezing temperature (Tf) and degree of thermal conductivity scaffolds with a range of pore sizes (60-350 μm) and degrees of alignment (longitudinal:transverse aspect ratios ~1:1 to 1.6:1) can be constructed. Fabricated by a forced evaporation process, CG scaffolds can display a densely-packed fibrillar structure with a consistent $\rho^*/\rho s$ (~75%); increasing the wt % of collagen in the CG suspension or volume of the CG suspension increases the membrane thickness ($p<0.05$) but not $\rho^*/\rho s$.

Cell and tissue function can be dependent on the three-dimensional scaffold morphology and/or the materials that make up the scaffold. Porosity of the three-dimensional scaffold should be adequate to provide enough space to allow a cell suspension to penetrate the structure. Additionally, texture, roughness, hydrophobicity, charge, and chemical composition are surface properties known to affect cell adhesion and subsequent cell behavior on a polymer surface and can be altered to benefit the types of cells or tissue that will be added to the scaffold.

The duration of scaffold of the invention is the length of time required for the scaffold to remain in a relatively solid-like form to, for example, give the cells or tissues within the scaffold to function to, for example regenerate skin at a wound site. The duration of a scaffold can be about 1 day, 2 days, 3 days, 4 days, 5 days, 6 days, 7 days, 10 days, 2 weeks, 3 weeks, 4 weeks, 5 weeks, 6 weeks, 7 weeks, 8 weeks, 3 months, four months or more.

The amount of collagen to glycosaminoglycan (w/w) can be about 99.5/0.5, 99/1, 98/2, 97/3, 96/4, 95/5, 94/6, 93/7, 92/8, 91/9, 90/10, 85/15; or 80/20. The average molecular weight between crosslinks can be about 1, 5, 10, 15, 20, 30, 40, 50, 60, 70, 80, 90, or 95 kDa. The average pore diameter can be about 1, 5, 10, 15, 20, 30, 40, 50, 60, 70, 80, 90, 100, 110, 120, 150, 200, 250, 300, 350, 400 μM or more. The pores can be random or can be in an axial arrangement (for use in, for example, nerve regeneration).

A scaffold can be in a variety of shapes including sheets, slabs, cylinders, tubes, spheres, or beads. A scaffold can also be provided in a shape that provides natural contours of a body part, e.g., a nose or nose part, an ear or ear part, a meniscus, etc. In one embodiment of the invention tubular scaffolds and scaffold plugs to insert within a tubular implant can be constructed to reconnect transected ends of a nerve.

In one embodiment of the invention, the scaffolds can be constructed of synthetic polymers such as polylactic acid (PLA, polylactide), its chiral derivative poly-L-Lactice (PLLA), polyglycolic acid (PGA, polyglycolide), ε-caprolactone (ε-CPL) and polycaprolactone, polyethylene (PE), poly(ethylene glycol) (PEG), and copolymers thereof. Inorganic materials such as calcium phosphates and bioactive glasses (45S5 Bioglass) can be used to make porous scaffolds for tissue engineering, in particular, bone tissue engineering constructs. Naturally derived ECM can also be used as scaffolds of the invention. Any of these scaffolds can replace the CG scaffolds discussed herein.

Biophotolithography

Surface-bound, covalently immobilized biomolecular concentration gradients, which can be useful in studying cellular behavior, are particularly difficult to generate, with many of the reported methods requiring specialized attachment chemistries, elaborate microfluidic designs, or complicated experimental configurations.

Furthermore, many of these methods only work for the immobilization of specific classes of biomolecules (peptides, proteins, carbohydrates, etc.) and are restricted in the number of different biomolecular species that can be simultaneously presented on a substrate, thereby limiting their general applicability to modeling complex in vitro environments.

Figure 1:
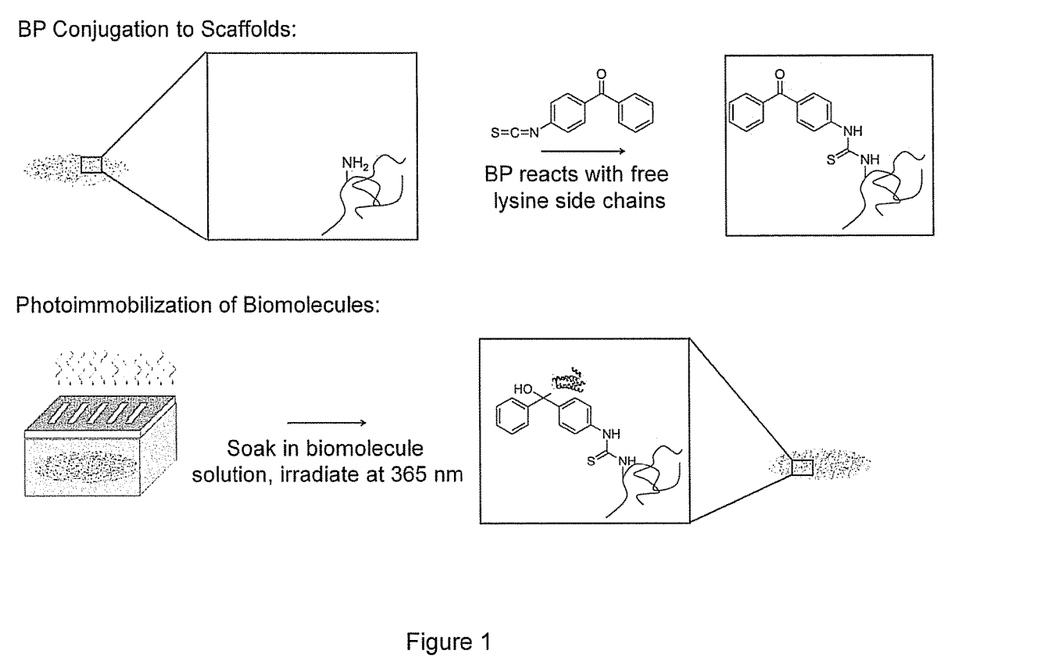
FIG. 1 shows BP conjugation and biomolecular conjugation. A) BP-isothiocyanate is conjugated through free amino-groups on the collagen-GAG scaffold. B) Scaffolds ore immersed in a biomolecular solution of interest and exposed to UV light. Covalent immobilization of biomolecules is dependent on the incidence of light.

To overcome these issues a direct and biomolecularly universal method for creating overlapping, multicomponent biomolecules patterns and surface gradients in three dimensional scaffolds based upon the solution phase photocrosslinking properties of benzophenone (BP) has been developed. Upon excitation with UV light, BP forms a transient diradical that can react with nearby C—H bonds from an adjacent biomolecule, forming a C—C covalent bond. Since the BP is surface immobilized, the new C—C bond represents a covalent tether between the biomolecule and the substrate. Importantly, if BP does not react with a nearby molecule within the excited state lifetime it relaxes back to the ground state from which it can be re-excited with subsequent optical pumping. Since the attachment occurs only where light is incident, geometric patterns and gradient of biomolecules can be generated by controlling the spatial exposure of light across the substrate (FIG. 1).

Upon illumination with about 350 nm to about 365 nm light, BP undergoes an n→π* transition to form a transient diradical that attaches to proximal biomolecules via insertion into a C—H bond. [43-45]. By conjugating BP to a 3D scaffold the biomolecules of interest can be immobilized to the scaffold. Additionally, multicomponent patterns can be created by spatially controlling the exposure of light onto the scaffold.

An important feature of BP photochemistry that makes it amenable to the creation of overlapping patterns is that excited BPs that fail to undergo C—H insertion relax back to the ground state whereby they can be re-excited in the presence of different solution-phase biomolecules. Because of the general reactivity of BP towards biomolecularly ubiquitous C—H bonds, this method represents a universal approach for direct surface bioconjugation. Immobilized biomolecular gradients, where the concentrations of multiple biomolecules are simultaneously controlled with continuous variation, are a common motif used in vivo to guide the growth and/or assembly of complex biological structures. Using BP-based photoimmobilization, overlapping gradients of multiple biomolecules can be created in either opposing or perpendicular configurations by simply placing a shutter attached to a programmable translation stage in the UV beam path. Furthermore, quantitative control over the amount and depth of biomolecular deposition can be achieved by varying either the light exposure or solution phase biomolecule concentration. The scaffold surface can be exposed to light for example for about 30 seconds, 1, 2, 3, 4, 5, 6, 7, 8, 9, 10, 20, 30 or more minutes (or any range between about 30 seconds and 30 minutes). Increased light exposure and increased concentration of biomolecules or a combination of both can lead to an increased depth of immobilization of the biomolecules into the 3D scaffold. A gradient of one or more biomolecules can be constructed on the surface of a 3D scaffold on the x, y axis or on the z axis (depth) or a combination of the x, y and z axes. For example, co-axial and co-axial and depth controlled gradients of two critical growth factors for BTI engineering can be generated.

A biomolecule to be immobilized to a 3D scaffold can be, e.g., one or more of peptides, proteins, carbohydrates, cytokines, hormones, nucleic acid molecules, integrins (e.g., alpha1beta1, alpha2beta1, etc.), antibodies, specific binding fragments of antibodies, biological samples such as blood, plasma, serum, or tissue homogenates. Proteins or polypeptides can be, for example, a growth factor, or any other type of protein that can stimulate the tissue regenerative process such as a proteoglycan, a glycoprotein, a cytokine, a cell-surface associated protein, a cell adhesion molecule (CAM), an angiogenic growth factor, an endothelial ligand, a matrikine, a matrix metalloprotease, a cadherin, an immunoglobin, a fibril collagen, a non-fibrillar collagen, a basement membrane collagen, a multiplexin, a small-leucine rich proteoglycan, decorin, biglycan, a fibromodulin, keratocan, lumican, epiphycan, a heparan sulfate proteoglycan, perlecan, agrin, testican, syndecan, glypican, serglycin, selectin, a lectican, aggrecan, versican, nuerocan, brevican, cytoplasmic domain-44 (CD-44), macrophage stimulating factor, amyloid precursor protein, heparin, chondroitin sulfate B, chondroitin sulfate A, heparan sulfate, hyaluronic acid, fibronectin, tenascin, elastin, fibrillin, laminin, nidogen/entactin, fibulin I, fibulin II, integrin, a transmembrane molecule, platelet derived growth factor (PDGF), an epidermal growth factor (EGF), transforming growth factor alpha, transforming growth factor beta, fibroblast growth factor-2 (FGF-2), thrombospondin, osteopontin, angiotensin converting enzyme (ACE), a vascular epithelial growth factor (VEGF), a bone morphogenic protein, a fibroblast growth factor, a growth differentiation factor, a platelet-derived growth factor, a placental growth factor, a transforming growth factor, an insulin-like growth factor, or combinations thereof.

In one embodiment of the invention, one or more biomolecules are added to the 3D scaffold in a solution. The concentration of the solution can vary such that the depth and amount of biomolecule that is immobilized to the scaffold is modulated.

Therefore, the invention provides methods of immobilizing one or more biomolecules onto a CG 3D scaffold comprising adding benzophenone to a collagen-glycosaminoglycan three-dimensional scaffold in the dark. "In the dark" is an absence of light. Optionally, instead of proceeding in the dark, the methods of the invention can be completed in an absence of light at a wavelength of about 350 to about 365 nm. A solution of one or more biomolecules added to one or more areas or over the entire CG 3D scaffold in the dark. The CG 3D scaffold is exposed to light at a wavelength of about 350 to about 365 nm, wherein the one or more biomolecules that are exposed to the light are immobilized onto the 3D scaffold. Optionally, one or more portions of the collagen-glycosaminoglycan three-dimensional scaffold can be exposed to the light while one or more other portions of the scaffold remain in the dark. Two or more biomolecules can be immobilized to the scaffold wherein the two or more biomolecules are immobilized onto the scaffold at two or more different depths into the scaffold. Biomolecules can be immobilized in the scaffold to a depth of about 1, 10, 25, 50, 75, 100, 125, 150, 200, 250, 300, 350, 400, 450, 500, 600, 700, 800, 900 µm or more (or any range between about 1 and about 900 µm or more).

Masks and Patterning

In one embodiment of the invention, a first mask is placed over the collagen-glycosaminoglycan three-dimensional scaffold prior to exposing the collagen-glycosaminoglycan three-dimensional scaffold to the light such that a pattern of one or more biomolecules is formed upon the 3D CG scaffold. A mask is a composition that partially blocks light from reaching the scaffold. It can comprise regions, e.g, holes, lines or other shapes, that allow light to reach the scaffold and regions that block light from reaching the scaffold. Optionally, the collagen-glycosaminoglycan three-dimensional scaffold can be placed back in the dark and the first mask removed from the collagen-glycosaminoglycan three-dimensional scaffold. Biomolecules that have not been immobilized to the scaffold can be washed away. One or more additional biomolecules can be added to one or more areas of the collagen-glycosaminoglycan three-dimensional scaffold in the dark. A second mask can be placed over the collagen-glycosaminoglycan three-dimensional scaffold in the dark. The 3D CG scaffold is again exposed to light at a wavelength of about 350 to about 365 nm and the second mask is removed. Additional masks can be placed on the 3D CG scaffold and additional biomolecules immobilized onto the scaffold in patterns over the surface of the 3D CG scaffold. The patterns can include different depths (z) for each of the one or more biomolecules immobilized to the scaffold as well as different distinct locations (x, y) on the scaffold. The result is a 3D CG scaffold with one or more biomolecules immobilized in distinct patterns (including co-axial and depth differences) over and in the scaffold.

In one embodiment, a mask, such as a chromium-coated quartz mask can be placed metal side down onto the scaffold and the scaffold irradiated for set time. The mask blocks portions of the scaffold from exposure to light. Following irradiation, scaffolds can be immersed in a buffer. For two or more component patterning, scaffolds can be washed and then incubated in a second biomolecule solution. The second biomolecule solution can be the same or different than the first biomolecule solution. A second mask is then placed on the scaffold. The second mask can block the same or different portions of the scaffold from exposure to light. Additional masks and biomolecules can be used for complex patterns. After immobilization, scaffolds can be stored in PBS.

Integration of Selectively Cleavable Moieties to Enable Temporal Regulation of Biomolecule Presentation The methods and compositions of the invention strategies can be further modified to enable temporal control over biomolecule display. Both exogenous (user-mediated) and endogenous (cell-mediated or other biologically-induced) release of biomolecules can be achieved. Cell-mediated release can be accomplished via, for example, the presence of a particular cell type (e.g., a cell type that expresses a protease that cleaves a linker) or density. Biologically-induced release can be accomplished, e.g., by changes in pH or other chemical cues that occur on or within the scaffold.

A biomolecule can be covalently linked to the scaffold through a cleavable linker. A cleavable linker is a linker that is capable of cleavage under various conditions. Conditions suitable for cleavage can include, but are not limited to acid-induced cleavage, light-induced cleavage (e.g., cleavable linkers comprising o-nitro benzyl groups), enzyme-induced cleavage, such as peptidase-induced cleavage or esterase-induced cleavage, temperature-induced cleavage, UV-radiation-induced cleavage, aqueous solution-induced cleavage (e.g., a water cleavable ester), disulfide bond cleavage, or combinations thereof. The desired biological effect can determine the choice of linker group.

In one embodiment, a cleavable linker can be cleaved by an enzyme, such as a matrix metalloprotease (MMP). Other enzymes that can cleave a cleavable linker include, for example, urokinase plasminogen activator (uPA), lysosomal enzymes, cathepsins, prostate-specific antigen, Herpes simplex virus protease, cytomegalovirus protease, thrombin, caspase, and interleukin 1-beta converting enzyme. Where the linker is cleaved by a protease, the cleavable linker can comprise a polypeptide molecule comprising a cleavage site for the protease.

A cleavable linker may be designed for cleavage in the presence of particular conditions or in a particular environment. Cleavage of such a linker may, for example, occur in the presence of particular pathological signals or a particular environment in a tissue or cell.

Exogenous (User-Mediated) Release of Biomolecules from the Scaffold

A wide range of release strategies can be used that rely upon exogenous chemical cues, such as pH, chemical oxidants, light, etc. Light offers the advantage of offering spatial control over a cleavage reaction within a CG scaffold. There are a number of potential photolabile moieties that have been utilized in solid phase synthesis [45]; most options either require release wavelengths that would damage cells in the scaffold ($\lambda \leq 320$ nm) or that overlap with the BP photoimmobilization reaction ($\lambda \approx 350\text{-}365$ nm). Fortunately, the rate of photocleavage is considerably slower than photoimmobilization; therefore a catch and endogenously triggered release strategy can be based upon the differential kinetics of these two processes.

In one embodiment of the invention, a photolabile moiety is a derivative of an o-nitrobenzyl group (also called a 2-nitrobenzyl group). A derivative of an o-nitrobenzyl group is or includes a substituted 2-nitrobenzyl moiety, examples include a 4,5-dimethoxy-2-nitrobenzyl (DMNB) group, a 4-methoxy-2-nitrobenzyl group, a 2-nitrobenzyl group, a 2-nitrophenylethyl (NPE) group, or a 1-(4,5-dimethoxy-2-nitrophenyl)ethyl (DMNPE) group.

Figure 4:
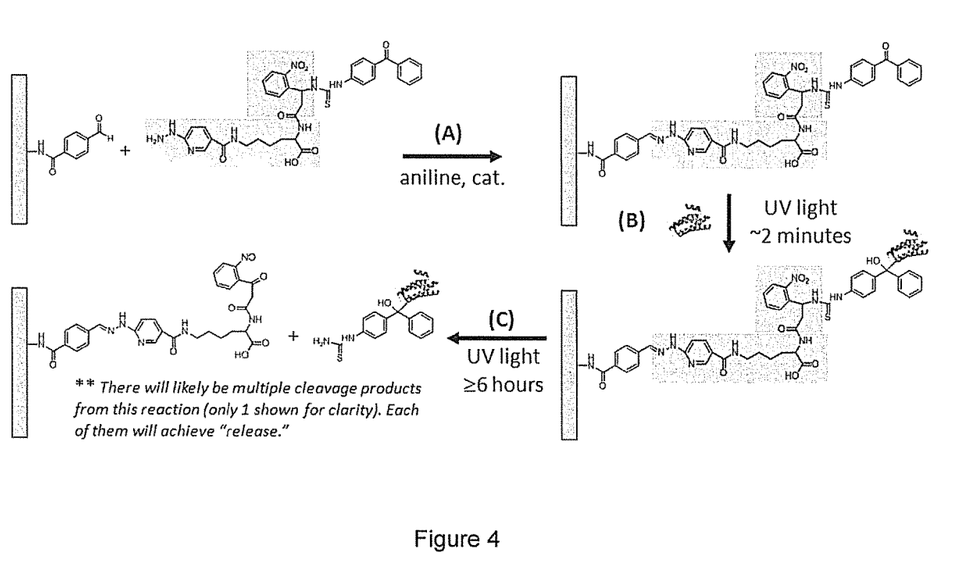

In one example, a photo-catch/photo-release scheme (FIG. 4) is based upon a tri-functional linker molecule that incorporates subunits capable of: 1) attaching to the surface of a CG biomaterial (e.g., a hydrazine-modified glycine that can link to, e.g., aryl aldehydes on the 3D scaffold); 2) BP-biophotoimmobilization, and 3) on-demand release of the immobilized biomolecule using light as a spatially controlled exogenous cue (e.g., nitrobenzyl-modified propionic acid). In one embodiment, a commercial hydrazine-modified lysine (BOC-protected hydrazine and FMOC-protected amine; Solulink) can be coupled to Wang resin, followed by the FMOC deprotection with piperidine in DMF. A commercial photocleavable 2-nitrobenzyl-modified β-alanine (Alfa-Aesar) can then be coupled and deprotected with piperidine. Next, BP-isothiocyanate can be attached to the N-terminal amine. Finally, the hydrazine can be deprotected using trifluoroaceteic acid (TFA), which will also serve to remove the trifunctional linker from the resin. The linker (FIG. 4) can be conjugated to 3D CG scaffolds via an aniline-catalyzed hydrazine bond formation reaction between the hydrazine and aromatic aldehyde functional groups that are preinstalled on the CG scaffold using a commercial succinimidyl ester reagent (Solulink). Once the linker is attached to the CG biomaterial, BP-biophotoimmobilization can be performed as described earlier in order to uniformly immobilize, e.g., rhodamine-labeled ConA (the biomolecule) to the entire surface of the scaffold, the success of which can be verified via fluorescent microscopy (loss of signal) as well as solution fluorimetry (gain of signal) can confirm the photochemical release strategy. Subsequently, the scaffold can be transferred to a PBS buffer solution and exposed through a photomask to low intensity UV light ($\lambda \approx 320\text{-}365$ nm) for long periods of time. A fluorescent streptavidin can be used if necessary to visualize release.

Nitrobenzyl groups are well established photocleavable subunits used in a range of synthetic applications, yielding o-nitrosocarbonyls after release. The complex structure of this trifunctional linker, while straight-forward to synthesize, makes it difficult to exactly predict the final product(s) of the photocleavage reaction. It is expected that multiple products might be generated, but all cleavage reactions will lead to the same important goal of exogenously cued biomolecule release.

As discussed above, light is an exogenous cue that affords spatial control over biomolecule release, particularly within CG scaffolds. Unfortunately, the relatively low energies of longer wavelengths of light are insufficient to drive photocleavage (or photoimmobilization) reactions, and photocleavage reactions at shorter wavelengths ($\lambda \leq 320$ nm) can cause significant damage to biomolecules and/or cells. However, it is possible to exploit significant differences between the rates of photoimmobilization (fast; ~2 minutes) and photocleavage (slow; hours) in order construct CG 3D scaffolds with exogenous linkers conjugated to biomolecules. Based upon rate differences it is expected that less than 1% of the linker molecules will be cleaved during the photopatterning step. Subsequently, the release step does not need to be exceptionally fast, since the timescale for cell infiltration is typically on the order of days. One additional potential concern would be that "released" biomolecules could re-immobilize to previously unreacted BPs. To alleviate this complication the surface can be blocked after photoimmobilization by crosslinking a non-specific molecule like bovine serum albumin to the remaining BPs via a second, short UV exposure.

Endogenous (Cell-Mediated) Release of Biomolecules from a Scaffold

For responsive biomaterials, it is desirable to harness endogenous cues of bioactivity in ways that would allow active feedback (positive or negative). For example, the secretion of certain factors might trigger the release of an immobilized growth factor, which would then diffuse away and thereby negatively regulate the process. Alternatively, a cue might liberate a siRNA that would then locally regulate only those cells that possess a specific functional phenotype, as determined by the secretion of the cue itself.

In one embodiment, a trifunctional linker that incorporates a peptide sequence that is a known substrate for matrix metalloproteinase-1 (MMP-1) can be used to cleave endogenously cued, responsive biomaterials from a scaffold. MMP-1 is significant in MSC biology in the context of BTI engineering, notably differential levels of MMP-1 expression in osteogenesis vs. tenocyte differentiation [46-48].

Using solid phase synthesis a tri-functional linker can be made that incorporates subunits capable of: 1) attaching to the surface of a CG scaffold; 2) BP-biophotoimmobilization, and 3) MMP-1 degradation. As with the photocleavable linker described above, a hydrazine-modified lysine can be coupled to a Wang resin and then a MMP-1-specific target amino acid sequence: PLALWAR is synthesized, via standard FMOC-based peptide synthesis. BP-isothiocyanate is then coupled to the N-terminal amine of the peptide. BOO deprotection of the hydrazine and release from the resin can be done in a single step using TFA.

The MMP-1 endogenously cued release mechanism can be verified independent of BP-biophotoimmobilization by synthesizing the same peptide substrate with the addition of a FAM-labeled lysine to the N-terminus. This trial linker molecule can be attached to aromatic aldehydes pre-installed onto 3D CG scaffolds and exposed to recombinant MMP-1 and appropriate co-factors. MMP-1 cued release will be observed via fluorescence microscopy (loss of signal) and solution fluorimetry (gain of signal). Alternatively, a FRET pair (DABCYL-EDANS) can be incorporated into the peptide on either side of the MMP-1 cleavage site. MMP-1 activity will release DABCYL, thus allowing the emission of EDANS to be visualized via fluorescent microscopy. The latter scheme has the advantage in that it is a "turn-on" observable. Experiments with the full tri-functional linker can be carried out in a similar fashion, except that rhodamine-labeled ConA can be photoimmobilized via BP-biophotoimmobilization prior to the introduction of MMP-1. The effect of MMP-1 concentration can be correlated with release rates from the CG scaffold surface. In addition to MMP-1 cleavage assays, the consequences of tissue inhibitors of matrix metalloproteinases (TIMPs) on this endogenously cued release system can be examined.

These strategies provide a universal method for creating multicomponent, overlapping patterns or gradients of biomolecules within a biomaterial with spatial and temporal control over presented surface densities.

Compositions

Scaffolds of the invention can be used for tissue regeneration. Alternatively, scaffolds of the invention can be used for in vitro studies, e.g., to study the activity of cells seeded on the scaffolds, to study cell attachment, gene expression, cell contraction, cell motility, etc. Compositions of the invention include collagen-glycosaminoglycan three-dimensional scaffold comprising one or more biomolecules covalently immobilized to the scaffold in a distinct pattern. A distinct pattern is an arrangement of biomolecules on the 3D scaffold (x, y, and/or z) where the biomolecules are present on some portions or areas of a 3D scaffold and not present at other portions or areas of the 3D scaffold. The two or more types of biomolecules can be covalently immobilized to the scaffold, wherein in each type of biomolecule is present in a unique distinct pattern. A unique distinct pattern means one biomolecule type or combination of biomolecule types are present in a first unique pattern, while a second biomolecule type or combination of biomolecule types are present in a second unique pattern that differs from the first unique pattern. Patterns may overlap, that is biomolecule A may be present at location 1, biomolecule B may be present at location 2 and both biomolecule A and biomolecule B may be present at location 3. Optionally, the one or more of the biomolecules can be immobilized to the scaffold via a cleavable linker, wherein the cleavable linker is cleavable by an exogenous cue or an endogenous cue. The collagen-glycosaminoglycan three-dimensional scaffold composition can be optionally seeded with cells or can be used without seeding with cells.

Methods of Use

One embodiment of the invention provides a method for tissue regeneration in a subject having a disorder characterized by tissue damage or loss comprising implanting or grafting a scaffold of the invention in or on the subject to induce tissue regeneration. For example, a scaffold of the invention, which has one or more biomolecules immobilized to it, can be implanted, with or without seeding the scaffold with cells, into the subject such that formation of tissue is induced.

Tissue regeneration, which is the enhancing of growth of new tissue, includes, for example, wound healing, and tissue augmentation (e.g., adding to existing tissue or enlarging a volume of a tissue).

A disorder characterized by tissue damage or loss includes any disorder, disease or condition comprising tissue damage or trauma (e.g., non-functional tissue, cancerous or pre-cancerous tissue, broken tissue, fractured tissue, fibrotic tissue, or ischemic tissue) or a tissue loss (e.g., due to trauma, infectious disease, genetic disease, or other disease) that would benefit from tissue regeneration. Examples of disorders or conditions requiring tissue regeneration include liver cirrhosis, diabetes, cystic fibrosis, bone cancer, bone damage, burns and wounds, age related macular degeneration, myocardial infarction, myocardial damage, heart valve damage, CNS lesions, nerve damage, peripheral nerve damage, spinal cord defects, articular cartilage defects, urological organ damage or degeneration, intestinal damage or degeneration, conjunctiva damage, bone and tendon interface damage or degeneration, cartilage damage, pancreatic tissue damage, liver tissue damage, and osteochondral defects.

Where cells are seeded onto the scaffold for ex vivo formation of a tissue the cells can be derived from the treated subject (autologous source) or from allogeneic sources such as embryonic stem cells that are not expected to induce an immunogenic reaction. Following ex vivo tissue formation the seeded scaffold is implanted in the subject.

One of skill in the art can determine when and how to implant the scaffold to induce tissue regeneration. For example, where the disease is damage to articular cartilage the scaffold can be seeded with chondrocytes. After 14-21 days in culture the scaffold can be implanted in subject at the articular surface of the joint.

Cells seeded onto the scaffold can be any type of cells such as a stem cell a human embryonic stem cell, a mesenchymal stem cell, a hematopoetic stem cell, a blood stem cell, an adult stem cell, an embryonic stem cell, a post-natal stem cell, a fetal cardiomyocyte, a cord blood stem cell, an autotransplanted expanded cardiomyocyte, a cardiomyocyte, a cardiac myoblast, a myofibroblast, an adipocyte, a totipotent cell, a pluripotent cell, a pluripotent mesenchymal stem cell, a synovial cell, a spinal disc cell, a tenocyte, a myoblast, a bone marrow cell, a mesenchymal cell, a parenchymal cell, an epithelial cell, an endothelial cell, a mesothelial cell, a fibroblast, a myofibroblast, an osteoblast, a chondrocyte, an exogenous cell, an endogenous cell, a pluripotent stem cell, a bone marrow-derived progenitor cell, a progenitor cell, a myocardial cell, a skeletal cell, a fetal cell, an embryonic cell, an undifferentiated cell, a multi-potent progenitor cell, a unipotent progenitor cell, a monocyte, a skeletal myoblast, a macrophage, a capillary endothelial cell, a xenogenic cell, and an allogenic cell.

A therapeutically effective amount of a scaffold of the invention is an amount of a 3D scaffold composition of the invention in sufficient strength such that the composition has a positive effect on the tissue that is being treated in the subject. The amount is therapeutically effective where the composition has an effect on the regenerative or wound healing activity at the site where the composition contacts tissue. A therapeutically effective amount can be determined by routine testing in patients with wounds or defects.

All patents, patent applications, and other scientific or technical writings referred to anywhere herein are incorporated by reference herein in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The following are provided for exemplification purposes only and are not intended to limit the scope of the invention described in broad terms above.

EXAMPLES

All reagents were purchased from Sigma-Aldrich (St. Louis, Mo.) unless otherwise noted.

Example 1: CG Scaffold Fabrication

CG scaffolds were fabricated via freeze-drying from a suspension of type I microfibrillar collagen from bovine dermis (Devro Inc., Columbia, S.C.) and chondroitin sulfate derived from shark in 0.05 M acetic acid [25]. This process has been previously optimized to produce a range of CG scaffold variants with a uniform pore microstructure with regular, polyhedral pores [1, 25, 26, 33, 34]. Briefly, a degassed CG suspension was added to an aluminum mold and placed in a freeze dryer (VirTis Genesis, Gardiner, N.Y.) at room temperature. The suspension was cooled at a constant rate (1.0° C./min) to −4° C. and held there for 2 hrs to allow the suspension temperature to equilibrate; the suspension was then further cooled to a final freezing temperature of −40° C. at 1.0° C./min, resulting in a continuous, interpenetrating network of ice crystals surrounded by the CG co-precipitate. Ice crystals were removed via sublimation under vacuum (200 mTorr) to produce a highly porous CG scaffold structure defined by individual fibers of CG content, termed struts. Scaffolds were dehydrothermally crosslinked and sterilized at 105° C. for 24 hrs under vacuum (<25 torr) in a vacuum oven (Welch, Niles, Ill.) prior to use [35].

Example 2: Chemical Attachment of BP to CG Scaffolds

A 20 mM solution of benzophenone-4-isothiocyanate containing 0.5 M N,N-diisopropylethylamine was prepared in dimethyl formamide (DMF) via an established method [36]. CG scaffolds were added to the solution and allowed to react at room temperature in the dark for 48 hrs. Scaffolds were thoroughly rinsed three times in DMF, 200 proof ethanol, and water (ELGA LabWater Reservoir, Veolia Water Systems, Buckinghamshire, UK) each for 1 hr; BP-tethered CG scaffolds were then stored under water and in the dark.

Example 3: Photoattachment of Biomolecules onto BP-Presenting CG Scaffolds

Biotinylated concanavalin A (ConA-biotin) was purchased from Vector Laboratories (Burlingame, Calif.), fibronectin (FN) was purchased from Invitrogen (Carlsbad, Calif.) and N-Cadherin (NC) was purchased from R&D Systems (Minneapolis, Minn.). Stock solutions of biomolecules were prepared by resuspending the lyophilized proteins in the manufacturer's recommended buffer solutions to a concentration of 1 mg/mL. For ConA-biotin and FN, the buffer was phosphate buffered saline, pH=7.4 (PBS); PBS containing $Ca^{2+}$ and $Mg^{2+}$ was used for NC. The solutions were aliquotted and stored at −20° C. Immediately prior to use, the stock solutions were diluted in the respective buffers to yield the empirically determined final solution concentrations of 5 μg/mL ConA-biotin or 100 μg/mL FN.

BP-modified scaffolds were placed onto a microscope slide and surrounded by a rubber o-ring. A 20 μL aliquot of protein solution was added to the top of the hydrated scaffolds and the chamber assembled by placing a glass coverslip on top. Scaffolds were soaked in protein solutions for 1 hr at room temperature prior to photoimmobilization. Photoimmobilization was then performed with an argon ion laser (Coherent Innova 90-4, Laser Innovations, Santa Paula, Calif.) with UV optics providing illumination at 351.1-363.8 nm. The Gaussian beam profile was shaped and expanded to give a uniform illumination of the scaffold using a π-shaper (Molecular Technologies, Berlin, Germany) and beam expanding optics. The uniformity of illumination was ensured using beam profiler (Ophir-Spiricon, Logan, Utah). The laser was adjusted to give a power of 20 $mW/cm^2$ at the illumination scaffold surface. For biomolecular patterning, a chromium-coated quartz mask was placed metal side down onto the chamber housing the CG scaffold and the substrate irradiated for set times varying from 30 sec to 5 min. Bulk exposure was achieved in the same way except without the photomask. Following irradiation, the scaffolds were immersed in a solution containing 0.2% pluronic F-127 in PBS for 1 hr. For 2-component patterning, scaffolds were subsequently washed for 1 hr in PBS and then incubated for 1 hr in the appropriate secondary component protein solution prior to a second patterning step, performed as described above. After immobilization, scaffolds were either stored in PBS prior to compositional analysis, structural characterization, and cell experiments, or were incubated in 1% (w:v) bovine serum albumin in PBS prior to microscopic visualization of biomolecular patterns.

Example 4: Fluorescent Visualization of Biomolecular Patterns

Biomolecularly patterned scaffolds were removed from the storage buffer and placed in a solution containing a fluorescently-labeled binding partner for at least 1 hr. Patterned ConA-biotin was visualized after incubation with a solution of 5 μM Qdot 525 conjugated streptavidin (Invitrogen, Carlsbad, Calif.) in 1% BSA-PBS. NC patterns were visualized with a pre-mixed cocktail of sheep anti-human NC (1 μg/mL, R&D Systems, Minneapolis, Minn.) and Alexa Fluor 647-conjugated donkey anti-sheep IgG (0.5 μg/mL, Invitrogen, Carlsbad, Calif.) in 1% BSA-PBS with $Ca^{2+}$ and $Mg^{2+}$. FN patterns were visualized with a pre-mixed cocktail of biotinylated rabbit anti-human FN (1 μg/mL, AbCam, Cambridge, Mass.) and Alexa Fluor 568-conjugated streptavidin (0.5 μg/mL, Invitrogen, Carlsbad, Calif.) in 1% BSA-PBS with $Ca^{2+}$ and $Mg^{2+}$. Two-component patterns were simultaneously stained for both protein components. After staining, scaffolds were rinsed in PBS prior to imaging on a LSM 710 confocal microscope (Carl Zeiss Microimaging, GmbH, Germany). Image analysis was performed using Imaris 7.0 (Bitplane AG, Zurich, Switzerland) to render 3D fluorescent images.

Example 5: Determination of Photoimmobilized Ligand Density

The amount of biomolecule photochemically attached to the scaffold was determined using a modified radioimmunoassay. Streptavidin was radiolabeled with [$I^{125}$] using Pierce iodination tubes (Pierce, Rockford, Ill.), and purified using spin filter columns (Biorad, Hercules, Calif.). The percentage of free [$I^{125}$] present in the sample was determined to be less than 3% and the concentration of protein in the sample was determined using a Bradford assay. Separately, a ConA-biotin-containing solution was introduced to the scaffolds before exposure (bulk, no patterning) for varying amounts of time. The modified scaffolds were then incubated with an excess of [$I^{125}$]-streptavidin for 1 hr before unattached streptavidin was removed by soaking in PBS for 1 hr. The scaffold was then covered with scintillation fluid (ScintiSafe Econo 1, Fisher Scientific, Pittsburgh, Pa.) and the total radioactive counts per minute were measured from the scaffold using a Beckman LS 6500 liquid scintillation counter (Beckman Coulter, Brea, Calif.). This value was then converted to the number of streptavidin molecules on the scaffold via the specific activity and the amount of bound ConA-biotin determined by assuming a 1:1 binding relationship.

The number of immobilized proteins was converted to a ligand density by dividing the number of conjugated molecules by the scaffold surface area as determined by cellular solids modeling. Cellular solids modeling has been a useful tool for the microstructural characterization of low density, open cell foams such as CG scaffolds [37]. The specific surface area (surface area/volume; SA/V) of the scaffold was calculated as a function of pore diameter (d) and the relative density (ratio of the scaffold density to the density of the solid material it is composed from:

$$\rho^*/\rho_s)[1]: \frac{SA}{V} = \frac{10.15}{d}\left(\frac{\rho^*}{\rho_s}\right)^{1/2}$$

Example 6 Microstructural, Mechanical, and Compositional Analysis

Scaffold Pore Size and Shape

Mean pore sizes and aspect ratios were calculated for CG and BP-tethered CG (CG-BP) scaffold variants to determine the effect of BP functionalization on CG scaffold microstructure. The size and shape of CG scaffold variants were determined via a previously described stereology approach [33]. Briefly, full thickness, 8 mm diameter samples were removed from the CG scaffolds with a biopsy punch (Miltex) and embedded in glycolmethacrylate. Longitudinal and transverse scaffold sections (5 µm thick) were cut on a microtome and stained with aniline blue to allow visualization of the CG strut network. Images were acquired from these specimens at 10× magnification on an optical microscope (Leica Microsystems, Germany) and analyzed using a linear intercept macro in Scion Image to determine both the mean pore size and the pore aspect ratio from a best fit ellipse representation of the average pore in each image.
Scaffold Mechanical Properties Tensile tests were performed on hydrated CG and CG-BP scaffolds in order to determine the effect of BP functionalization on scaffold mechanical properties. Tests were performed on rectangular scaffold samples (8 mm×25 mm×3.5 mm thick); scaffolds were hydrated in PBS for 24 hrs and then tested in tension with an MTS Instron 2 (Eden Prairie, Minn.) using rubberized grips to prevent sample slip. Scaffolds were pulled to failure at a rate of 1 mm/min; scaffold tensile elastic modulus ($E_{s,\ tension}$) was calculated from the slope of the stress-strain curve over a strain range of 5-10% [37].
Scaffold Composition X-ray diffraction (XRD) analyses were used to determine whether any significant changes in the crystallinity or chemical nature of the CG scaffold occurred with BP functionalization; XRD has previously been used to quantify CG scaffold composition following integration of variable levels of mineral content (0-80 wt %) [22]. XRD analyses were performed using a Cu Kα radiation source with a Rigaku D-Max diffractometer. Diffraction patterns were acquired using a step size of 0.028° 2θ and a dwell time of 10 s.
Cell Culture and Scaffold Seeding MC3T3-E1 mouse clonal osteogenic cells were cultured in standard culture flasks in α-MEM supplemented with 10% fetal bovine serum, 1% L-glutamine, and 1% penicillin/streptomycin. Cells were fed every 3 days and cultured to confluence at 37° C. and 5% $CO_2$. Prior to each experiment, full-thickness (3.5 mm thick), 6 mm diameter CG scaffold samples were cut with a biopsy punch (Miltex) and then hydrated (>1 hr) in culture media. MC3T3-E1 cells were then trypsinized and resuspended at a concentration of $3×10^5$ cells per 20 µL media or 1×PBS. $1.5×10^5$ cells in 10 µL media were seeded onto each side of the hydrated scaffold disks in a previously described manner [3] to a final concentration of $3×10^5$ cells per scaffold. Cell-seeded scaffolds were then incubated in ultra-low attachment 6-well plates (Corning Life Sciences, Lowell, Mass.) at 37° C. and 5% $CO_2$ for the duration of all experiments. For longer (>30 min. attachment) experiments, 4 mL of supplemented α-MEM was added to each well and changed every 3 days.

Example 8: Quantifying Cell Attachment

A previously developed cell attachment assay was used to determine the total number of cells attached to the scaffold [1]. At each time point, scaffolds were first washed in PBS to remove any unattached cells and then placed in a papain solution to digest the scaffold and lyse the cells to liberate their DNA. A Hoechst 33258 dye (Invitrogen, Carlsbad, Calif.) was used to fluorescently label double-stranded DNA [38] and fluorescence levels from each sample were read using a fluorescence spectrophotometer (Varian, Santa Clara, Calif.): 352 nm excitation, 461 nm emission. Experimental readings were then compared to a standard curve created by measuring the fluorescence levels for a range of known cell numbers to determine cell attachment at each time point as a percentage of the total number of seeded cells.

Example 9: Characterizing Cell Bioactivity

A non-destructive alamarBlue approach was used to compare the metabolic activity of the cells in each cell-seeded scaffold over time. Healthy cells continuously reduce resazurin, the active ingredient in alamarBlue, to the highly fluorescent compound resorufin; consistent exposure times enable comparison of the gross metabolic activity in each cell-seeded construct. Cell-seeded scaffolds were incubated at 37° C. in alamarBlue (Invitrogen, Carlsbad, Calif.) solution with gentle shaking for 120 minutes [39]. Resorufin fluorescence was read at 570 nm excitation and 585 nm emission using a fluorescent spectrophotometer. A standard curve was created by measuring the metabolic activity of a range of known cell numbers. Scaffold fluorescence readings were interpolated on this curve to express results as a percentage of the total number of seeded cells.

Statistical Analysis

One-way analysis of variance (ANOVA) was performed on cell bioactivity, cell number, and mechanical data sets respectively followed by Tukey-HSD post-hoc tests. Paired student t-tests were used to compare CG and CG-BP scaffold pore size and shape. Significance was set at p<0.05. At least n=6 scaffolds were analyzed at each time point for cell bioactivity while n=6 scaffolds were digested and assayed at each time point for cell number. Each group for mechanical tests contained n=6 scaffolds. Pore size and shape analysis was performed on transverse (n=3) and longitudinal (n=3) scaffold sections from each scaffold variant (36-54 discrete cross-sectional histology images). Error is reported as the standard error of the mean unless otherwise noted.

Example 10: Visualization of Biomolecularly Patterned CG Scaffolds

Throughout, CG scaffold variants will be referred to as CG, CG-DMF, CG-BP, and CG-BP-X for unmodified CG scaffolds, CG scaffolds that have been exposed to the DMF solvent (but without BP conjugation), CG scaffolds with conjugated BP, and CG-BP scaffolds with photo-immobilized biomolecule X, respectively.

Single component ConA-biotin patterns of 100 µm stripes with 400 µm spacing, and the script "I" logo of the University of Illinois at Urbana-Champaign were visualized using confocal fluorescence microscopy. Patterns were clearly discernible from the background indicating successful photoimmobilization of ConA-biotin via the benzophenone groups presented on the CG scaffold. Multi-component patterns of FN and NC were photopatterned in two steps by sequential exposure of each biomolecule through the same photomask utilized for one component patterns. NC was patterned first (horizontal) followed by FN (vertical) with a 90° rotation of the photomask between exposures.

Fluorescence microscopy approaches were used to validate the creation of a range of biomolecules patterns within CG scaffolds. First, a single-phase, discrete geometric pattern was created in the form of repeating stripes (100 µm wide, 400 µm periodicity) of photoimmobilized ConA-biotin, visualized via Qdot 525 conjugated streptavidin. Conversely, areas in between the stripes where UV light was blocked by the photomask are not fluorescent since the BP molecules were not excited and thus did not conjugate ConA-biotin. The technique was also successfully used to create a non-geometric pattern of ConA-biotin in the form of the University of Illinois script "I" logo. Again, a clear contrast was observed between areas exposed to light define the pattern while fluorescence is not observed from the areas blocked during illumination. Taking advantage of the depth profiling capability of confocal microscopy it was determined that currently BP photopatterns can be created to a depth of 300 µm into the scaffold (data not shown). Although the high porosity of the CG scaffold allows for reasonable patterning depths.

Sequential exposures of BP-presenting scaffolds in the presence of different biomolecules allow for the construction of multi-component patterns. For example a CG-scaffold patterned with vertical 100 µm stripes of FN and horizontal 100 µm stripes of NC was created. Notably, both FN and NC are co-immobilized at the intersections of the two stripe patterns, highlighting an interesting property of BP-photoattachment strategy as opposed to other schemes that rely upon deprotection or unmasking of reactive groups [43, 44]. Because the diradical formed with UV light has a finite lifetime (~180 µsec) after which it relaxes back to the ground state [45], if an excited BP fails to react with a solution phase biomolecule it can be re-exposed in the presence of a second biomolecule, which allows for the creation of overlapping patterns. The relative yield of these photoreactions can be controlled by exposure intensity and time, as well as the solution-phase biomolecule concentration, since the number of molecules in solution dictates the probability of interaction while the BP is in the excited state [32]. The conditions used for two component patterning were controlled so that the first component exposure did not saturate the scaffold, facilitating the construction of overlapping patterns. Alternatively, additional BP can be added to the scaffold prior to the addition of more biomolecules to the 3D scaffold. Importantly, the ability to control the presented concentration of multiple biomolecules at a single spatial location will be of tremendous utility in downstream applications. The selection of FN and NC for two-component patterning was strategic in that both proteins are implicated in the proliferation and maintenance of the MC3T3 osteoblast-like cells used in these experiments [46, 47]. Multi-component biomolecule patterns can be particularly useful for engineering biomaterial mimics of tissue interfaces (e.g. osteochondral, ligament-bone, and tendon-bone) where the sub-millimeter gradients of chemical and mechanical properties found in vivo are difficult to recapitulate in synthetic model systems [48]. For example, growth factor agonists of tenocyte and osteoblast can be immobilized into tendinous and osseous compartments of a multiphase CG scaffold. ECM proteins aggrecan and decorin can also be biophotoimmobilized at the interfacial zone of these same materials. Region-specific high concentration of native ECM proteins are difficult to fabricate via freeze drying approaches, but may have significant benefit for regenerative medicine applications.

Example 11: Determining the Amount of Biomolecular Immobilization

Using cellular solids modeling tools to calculate scaffold specific surface area and a modified radioimmunoassay to determine the total amount of ConA-biotin immobilized to the scaffold surface, the surface density of this representative biomolecule bound to the CG scaffolds was determined to be approximately 1000 molecules/$\mu m^2$ for maximum loading conditions.

Example 12: Scaffold Microstructural Analysis

CG and CG-BP scaffolds were determined to have mean pore sizes of 86.6±9.8 µm and 77.1±9.7 µm (mean±standard deviation) as well as mean pore aspect ratios (ratio of pore size for longitudinal vs. transverse sections taken from the scaffold) of 1.05±0.03 and 1.06±0.03, respectively. No significant difference was observed in scaffold mean pore size (p=0.13) or aspect ratio (p=0.32) for CG versus CG-BP scaffolds. No significant difference was observed in scaffold pore size in the longitudinal versus transverse planes for CG and CG-BP scaffolds (p=0.14, 0.66 respectively). These pore diameters and longitudinal:transverse aspect ratios were also similar to previously characterized CG scaffolds fabricated via similar freezing conditions [1].

Example 13: Mechanics of CG, CG-DMF, and CG-BP Scaffolds and Scaffold Compositional Analysis The DMF treatment stage of the BP functionalization process was observed to significantly increase scaffold tensile modulus (p=0.0005). The tensile modulus of CG scaffolds alone (54.7±12.5 kPa; mean±standard deviation) was significantly lower than that of the CG-DMF (87.6±18.4 kPa) and CG-BP (102.8±17.6 kPa) variants; no significant difference was observed between the tensile modulus of the CG-DMF and CG-BP scaffolds (p=0.16).

Characteristic XRD patterns for the CG, CG-BP, and CG-BP-FN scaffolds were observed. All three variants display a broad peak at 2θ=20° representing the characteristic interchain spacing of the collagen triple helix [40]. No sign of collagen denaturation (loss of the broad collagen peak) was observed for any of the samples; the increase in peak height for the CG-BP and CG-BP-FN variants is indicative of increased crystallinity of the samples relative to the original CG scaffold likely due to a crosslinking effect from DMF exposure, consistent with the observed increase in scaffold tensile modulus.

Quantitative analysis of scaffold microstructural, mechanical, and chemical composition revealed that the processing steps required for BP conjugation to the CG scaffold induced some quantifiable changes in scaffold properties, but not in a manner that would suggest a negative biological response. Scaffold microstructure (pore size, pore aspect ratio), a key parameter in determining overall scaffold bioactivity, was not influenced by BP conjugation. Exposure of the CG scaffold to the DMF buffer required to mediate BP conjugation likely increased the crosslinking density of the CG scaffold, as reflected by the increase in scaffold tensile modulus and material crystallinity (XRD). However, XRD spectra did not exhibit a peak shift characteristic of collagen gelatinization. These results suggest that the DMF buffer additionally crosslinks the CG scaffold, imparting improved mechanical properties, but does not fundamentally alter scaffold microstructural or compositional properties; in the future we can, adjust the crosslinking of CG scaffolds [25] to mimic the crosslinking effect of CG-BP scaffold variants in order to allow for additional comparative experiments. These results also suggest that photopatterning of biomolecules to the BP functionalized scaffold does not additionally alter scaffold properties; no change in scaffold modulus or material crystallinity was observed due to FN functionalization to the BP.

Example 14: MC3T3-E1 Viability in CG-BP Scaffolds

Figure 2:
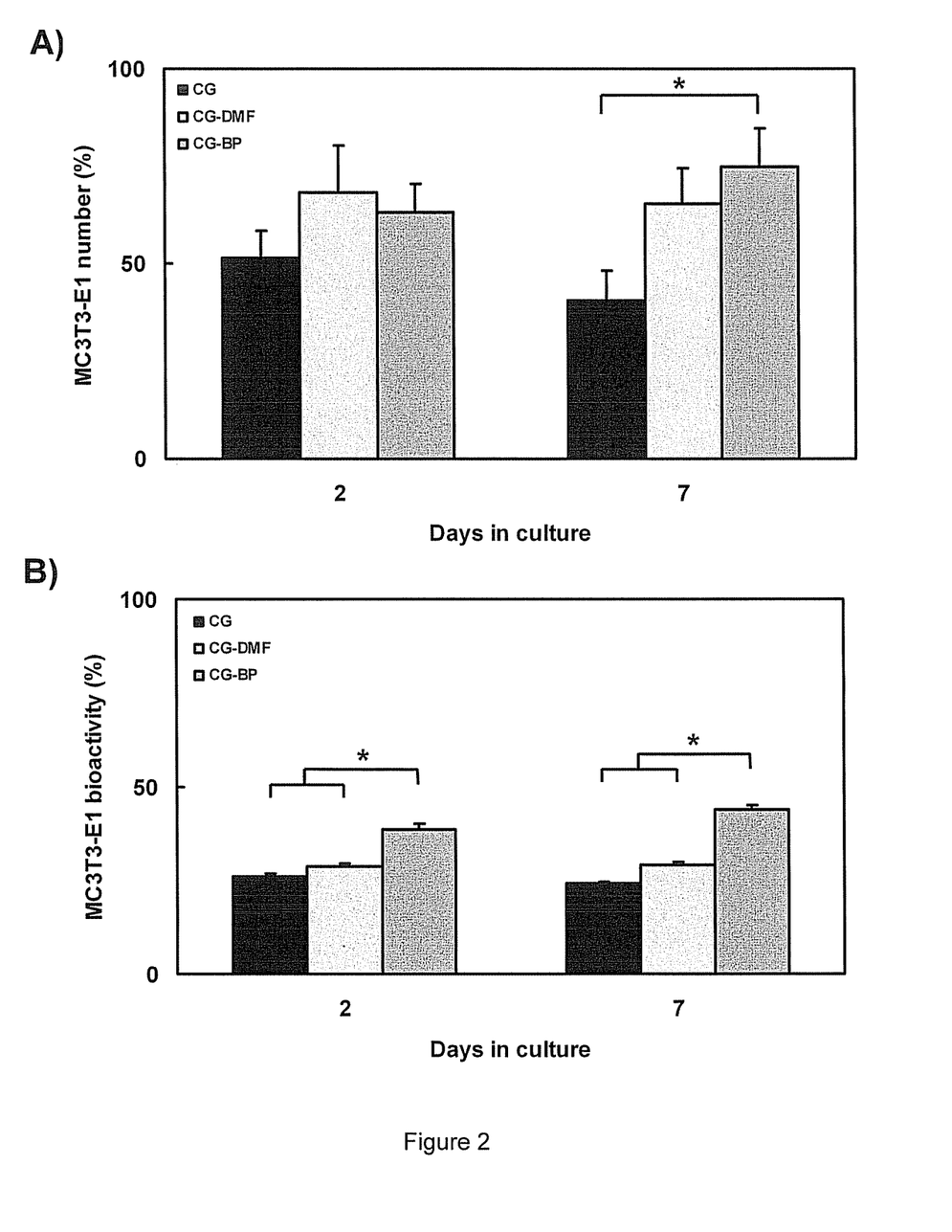
FIG. 2 shows metabolic activity and cell attachment in modified scaffolds. A) MC3T3-E1 attachment in CG, CG-DMF, and CG-BP scaffolds after 2 and 7 days of in vitro culture. B) MC3T3-E1 bioactivity CG, CG-DMF, and CG-BP scaffolds after 2 and 7 days of in vitro culture. Conjugation of BP to the scaffolds or DMF exposure does not adversely affect cell activity or attachment.

The long term viability of MC3T3-E1 cells on CG, CG-DMF, and CG-BP scaffolds was determined for up to 7 days of in vitro culture in complete α-MEM media in order to confirm that the BP immobilization process did not impart any inherent cytotoxicity. One-way ANOVA indicates significant differences in cell metabolic activity via alamarBlue assay at both day 2 and day 7 between the three groups (p<0.0001) with the CG-BP group showing significantly higher bioactivity at both time points compared to the CG group (day 2: p=0.0002, day 7: p<0.0001). While there are no significant differences in total number of attached cells as determined via DNA assay at day 2 (p=0.44), the CG-BP group showed significantly higher cell attachment at day 7 (p=0.04) (FIG. 2). These data suggest that the BP functionalization process does not have a negative impact on the native bioactivity of CG scaffolds.

After demonstrating that CG scaffolds could be patterned using BP-based photolithography methods without significant deterioration of physical properties, the effect of BP conjugation to CG scaffolds on overall material bioactivity was examined. Even though extensive washing steps were utilized, no decrease in MC3T3-E1 pre-osteoblast number or metabolic activity was found out to 7 days of culture in CG-DMF or CG-BP scaffolds relative to unmodified CG scaffolds (FIG. 2). These data indicate that BP conjugation and the organic solvents used in this process do not adversely influence cell attachment, bioactivity, and proliferative potential. The observed increase in MC3T3 number and bioactivity for CG-BP scaffolds relative to CG control is in fact likely due to differences in scaffold modulus.

Example 15: MC3T3-E1 Attachment and Bioactivity in CG-BP-FN Scaffolds

Figure 3:
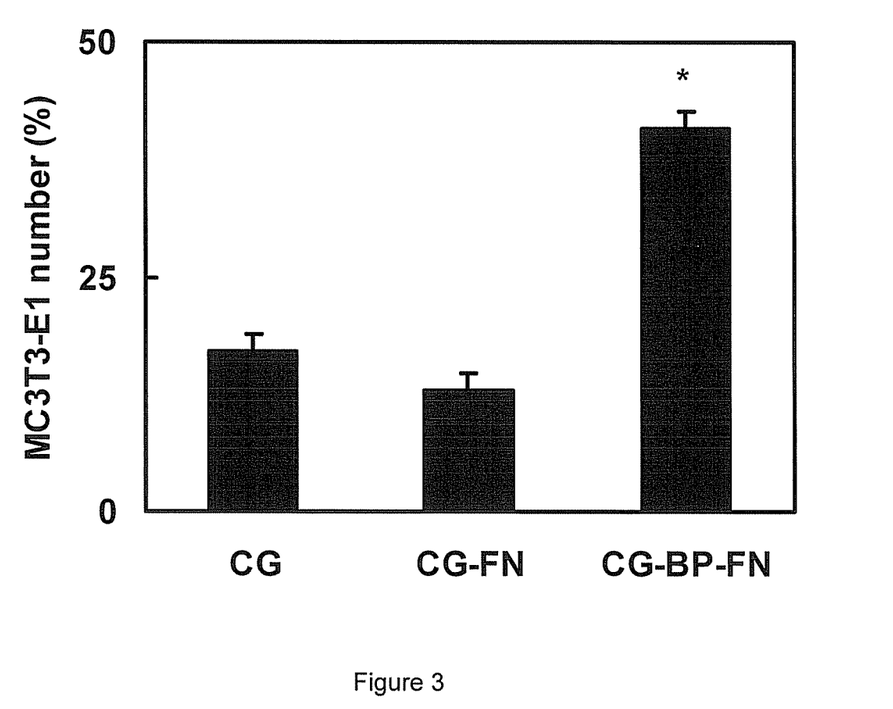
FIG. 3 shows a cell attachment assay. CG-BP-Fn scaffolds showed significantly higher MC3T3-E1 attachment compared to the control bare CG and CG-Fn scaffolds after 30 min.

Fibronectin is the key adhesion ligand required to mediate early (<1 hr) cell attachment to CG scaffolds [41]. Here, MC3T3-E1 cell attachment was assessed after 30 min in CG, CG-BP-FN, and CG-FN (unmodified CG scaffold soaked in the FN solution used to create CG-BP-FN scaffolds and then washed in PBS) scaffolds to assess the relative ability for BP functionalized CG scaffolds to alter the innate bioactivity of the CG scaffold. The MC3T3-E1 cells were washed and resuspended in PBS prior to being seeded into PBS hydrated scaffold variants, and the entire experiment was performed in PBS in order to prevent non-specific adsorption of exogenous factors from the α-MEM media, thereby insuring that any change in cell attachment was due to the covalent immobilization of fibronectin rather than additional soluble proteins from the α-MEM media. Fibronectin treatment was observed to have a significant effect on early MC3T3-E1 attachment (p<0.0001) (FIG. 3). Scaffolds with BP-immobilized fibronectin (CG-BP-FN) showed significantly higher levels of cell attachment after 30 min relative to CG scaffolds alone (CG, p<0.0001) or CG scaffolds with passively adsorbed FN (CG-FN, p<0.0001); no significant difference was observed in initial cell attachment for CG versus CG-FN groups (p=0.12), suggesting non-specific FN adsorption to the CG scaffold does not mediate initial cell attachment.

CG scaffold microstructure plays a significant role in influencing cell attachment [1, 50] and cell attachment to the scaffold is mediated by sequential utilization of vitronectin, fibronectin and collagen binding motifs [41]; however the fibronectin binding motif was specifically implicated in mediating the initial cell attachment events to the CG scaffold within the first 2 hours after cell-seeding prior to formation of stable attachments directly to the collagen structure [41]. Here we examined the fraction of MC3T3-E1 preosteoblasts adhered after only 30 min to untreated CG scaffolds versus BP-conjugated CG scaffolds where we covalently immobilized fibronectin via photolithographic attachment to the entire scaffold (CG-BP-FN). As an additional control, we also tested CG scaffolds that were soaked in a fibronectin solution (CG-FN) and then washed in PBS, where passive FN physiosorption was the only mechanism for surface patterning. The cell attachment study was performed in PBS rather than media to prevent nonspecific adsorption of additional proteins from the media that could alter cell adhesion profiles. No significant difference in cell attachment was observed for the CG versus FN-physiosorbed CG scaffold, while a greater than two-fold (p<0.0001) increase in MC3T3-E1 cell attachment was observed for the CG-BP-FN scaffold versus the CG or CG-FN scaffolds (FIG. 3). These data demonstrate that BP photolithography can be used to immobilize biomolecules to CG scaffolds in order to elicit a specific biological response. These results also demonstrate the advantage of covalent immobilization (CG-BP-FN) rather than physical adsorption (CG-FN) of fibronectin to mediate initial cell attachment events within 3D biomaterials. Furthermore, preliminary results indicate that cells do preferentially adhere specifically to regions displaying adhesion ligands patterned within CG-BP scaffolds over areas that were not exposed to light during the immobilization process. A further advantage of this approach is that BP photopatterning at high surface densities allows the sampling of a wide range potential biomolecule conformations. While not able to present a specific FN conformation, the C—H bond insertion mechanism that links the biomolecule (i.e. FN) to the scaffold via BP is not biased towards any particular C—H bonds and therefore it is almost certain that proteins are immobilized in random orientations across the surface. On a cellular length scale, which is significantly larger that the biomolecular length scale and the spacing between BP molecules on the scaffold surface, there statistically are likely many proteins that have a suitable configuration to engage cellular receptors [32].

Therefore, BP photolithography methods can be applied to 3D biomaterials in order to spatially pattern immobilized biomolecules in the CG scaffold structure, and that these factors can induce a resultant change in cell bioactivity in response to factor presentation.

Conjugation of benzophenone to CG scaffolds and the photochemical generation of patterns of biomolecules in a controlled and spatially well-defined manner has been demonstrated. Since this immobilization approach only requires the presence of a C—H bond, it is biomolecularly general and has broad applicability to a range of classes of biomolecules. The method offers a direct, photolithographic approach to generate complex, multi-component patterns or gradients of biomolecules to more accurately mimic the heterogeneity of the native ECM using biologically mimetic collagen scaffolds. Importantly, this process allows separating scaffold fabrication, biomolecule patterning, and cell seeding steps, thereby increasing the potential for independent factor modulation as well as reducing the potential for adverse (cytotoxic) effects on cell behavior due to fabrication and patterning.

Example 16

Creation of Functional Patterns of Two Complex Biomolecules, Proteoglycans and Growth Factors, for a Precursor BTI CG Biomaterial Accurate prediction of bioactive concentrations of matrix-bound biomolecules from bioactive solution concentrations is poorly understood, but tools are provided herein to rapidly assess the significance of discrete biomolecule patterns on cell bioactivity. Multiphoton biophotoimmobilization can be used for creating complex 3D patterns (islands, coaxial distributions) of growth factors for studies of, e.g., tendon repair.

Soluble PDGF-BB and IGF-1 improve tenocyte proliferation and metabolic capacity; however, accurate prediction of bioactive concentrations of matrix-bound biomolecules from bioactive solution concentrations is poorly understood. Single component (PDGF-BB or IGF-1) gradients on 3D scaffolds can be used to identify ranges of biomolecules concentration that elicit biological responses. Two-component, orthogonal biomolecular gradients of PDGF-BB and IGF-1 that span the entire space of functional surface concentrations can then be used to identify optimal co-expression concentrations that improve tenocyte viability, proliferation, and matrix synthesis. Primary equine tenocyte viability and proliferation can be quantified via DNA content and MTS assays; tenocyte metabolic activity can be determined via AlamarBlue assays [49]. The total amount and type of newly synthesized collagen can be quantified via ELISA or 3H proline assays [50-51]. Gene expression can be quantified via qPCR using a library of PCR primers [52] or via equine gene microarrays [53]. In addition to the significant ECM variation between the tendinous and osseous compartments of the BTI and the gradient in ECM alignment as well as mineral content and crystallinity within the interface, the interfacial region also contains distinct proteoglycans. Aggrecan and decorin are found in high concentrations within the interface, with more decorin found on the tendon side and more aggrecan on the bone side [54]. While multicompartment scaffolds with distinct interfaces can be made via freeze-drying [23], creating regional localizations and biomolecules subpatterns can be quite difficult, particularly for hydrophobic proteoglycans. The patterning methods of the invention can solve this difficult problem. The BP-biophotoimmobilization of the invention can be used for patterning decorin and aggrecan on CG scaffolds and to create two-component, opposing biomolecular gradients of decorin and aggrecan.

Primary porcine (Yorkshire pig) adipose derived mesenchymal stem cells (pADMSCs) can be isolated and via liposuction and subsequent high-volume cell sorting [55]. MSCs can be cultured on the opposing gradients to evaluate the effect of decorin:aggrecan ratio on MSC bioactivity, notably induced tenocyte vs. osteoblast vs. fibrocartilage cell phenotypes. MSC viability and proliferation can be quantified via DNA content and MTS assays; metabolic activity can be determined via an AlamarBlue assay [49]. MSC differentiation state can be quantified by qPCR; quantity and type of new matrix synthesis will be determined from H & E histology sections [56].

Use Multi-Photon Strategies to Control Biomolecule Presentation in Three Dimensions Both the lateral (x, y) and depth (z) resolution and maximal achievable depth of BP-biophotoimmobilization can be improved by utilizing two-photon excitation of BP. Two-photon lithographic methods can impart high feature resolution since two photon absorption, which drives the patterning process, depends quadratically on intensity. Therefore, absorption (patterning) occurs only in a very localized volume when a highly focused laser source is used. Furthermore, two-photon patterning can also increase the depths to which patterning can be achieved within a solid support as longer wavelengths of light are less efficiently scattered then are shorter wavelengths.

Two-Photon BP-BioPL Facilitates Depth Control Over Biomolecular Immobilization.

Using a LSM 710 multi-photon confocal microscope with $\lambda$=720 nm excitation from a SpectraPhysics Mai Tai® DeepSee™ Ti:sapphire laser and 70 fs (femtosecond) pulses 3D patterns of ConA-biotin were created within an isotropic CG scaffold, notably a series of four rectangular prisms patterned sequentially deeper into the scaffold. Each rectangular prism was 450×450×100 µm. The first prism was patterned at the CG scaffold surface and each subsequent prism was patterned at a depth of 50 µm lower than the previous.

Generation of Co-Axial Distributions of Critical Growth Factors for BTI Engineering within Anisotropic CG Scaffolds Cell motility in 3D is often mediated by gradients in matrix-bound biomolecules [57]. Anisotropic CG scaffolds that mimic the native ECM of tendon can support long-term tenocyte culture and solution-phase PDGF-BB and IGF-1 can be used to increase tenocyte proliferation and metabolic activity within these structures. Co-presentation of PDFG-BB and IGF-1 can effect primary equine tenocyte localization, viability, proliferation, and matrix synthesis. The effect can be examined by creating two distinct 3D biomolecule patterns and assessing their effect on tenocyte recruitment and bioactivity.

3D 'islands' (rectangular prisms) of PDGF-BB immobilized within an isotropic CG scaffold substrate can be created. Islands size can be varied in size from the scale of an individual tenocyte (~50 µm) to a large group of tenocytes (~750 µm); island PDGF-BB density can be varied over the a range. After seeding primary tenocytes within these microstructurally uniform but biomolecularly patterned scaffolds, the difference in local cell density and proliferation kinetics within and outside the island regions can be assessed. Cell number and spacing can be quantified via confocal microscopy the kinetics of cell proliferation can be measured globally via MTS assays and locally via CFSE cell tracing experiments [58].

Co-Axial Distributions of PDFG-BB and IGF-1

A co-axial pattern (PDGF-BB central core; IGF-1 outer jacket) can be created along the length of cylindrical plugs (2 mm dia, 10 mm long) of an anisotropic CG scaffold variant (Tf −40° C.: 90 µm pore size, 1.6:1 longitudinal: transverse pore size ratio). Patterns can be created that enable sequential utilization of biomolecular cues for engineering anisotropic tissues such as tendon. While PDGF-BB and IGF-1 can similarly increase overall tenocyte recruitment into CG scaffolds, PDGF-BB induces a significantly greater increase in tenocyte metabolic activity, a key requirement in the central core of a biomaterial. Primary tenocytes can be cultured in these patterned scaffolds for up to two weeks. Global tenocyte number, bioactivity, and matrix biosynthesis can be determined via methods described above. Longitudinal and transverse histology sections can be used to assess the relative number and distribution of tenocytes within the central core and outer jacket regions along the entire length of each construct. It is expected that the addition of a central PDGF-BB core will: 1) globally significantly increase the tenocyte number and mean metabolic activity within the entire scaffold; and 2) it will specifically increase the number of tenocytes within the central core region of the patterned scaffolds.

REFERENCES

[1] O'Brien et al., Biomaterials. 2005; 26:433-41.
[2] Yannas et al., Proc Natl Acad Sci USA. 1989; 86:933-7.
[3] Harley et al., Biophys J. 2008; 95:4013-24.
[4] Tse et al., PLoS ONE. 2011; 6:e15978.
[5] Engler et al., Cell. 2006; 126:677-89.
[6] Zaman et al., Proc Natl Acad Sci USA. 2006; 103:10889-94.
[7] Shen et al., Acta Biomater. 2008; 4:477-89.
[8] Capito et al., Gene Ther. 2007; 14:721-32.
[9] Mikos et al., Tissue Eng. 2006; 12:3307-39.
[10] Engelmayr et al., Nat Mater. 2008; 7:1003-10.
[11] Wopenka et al., Appl Spectrosc. 2008; 62:1285-94.
[12] Moffat et al., Proc Natl Acad Sci USA. 2008; 105:7947-52.
[13] Lutolf et al., Nat Biotechnol. 2005; 23:47-55.
[14] Huebsch & Mooney, Nature. 2009; 462:426-32.
[15] Huang & Ding, Soft Matter. 2010; 6:3395-401.
[16] Harley & Gibson, Chem Eng J. 2008; 137:102-21.
[17] Harley et al., J Biomed Mater Res A. 2010; 92:1066-77.
[18] Harley et al., J Biomed Mater Res A. 2010; 92:1078-93.
[19] Harley et al., Acta Biomater. 2007; 3:463-74.
[20] O'Brien et al., Technol Health Care. 2007; 15:3-17.
[21] Liu et al., Bone. 2006; 39:825-36.
[22] Xu et al., J American Chemical Society. 2009; 131:797-803.
[23] Song et al., J American Chemical Society. 2009; 131:1340-1.
[24] Irimia et al., Lab on a Chip. 2006; 6:191-8.
[25] Toh et al., Langmuir. 2009; 25:8894-8.
[26] O'Brien et al., Biomaterials. 2004; 25:1077-86.
[27] Haugh et al., Tissue Eng Part C Methods. 2010; 16:887-94.
[28] Harley et al., Cells Tissues Organs. 2004; 176:153-65.
[29] Sinsheimer J et al., J Pharm Sci. 1975; 64:925-30.
[30] Gibson et al., Cambridge, U.K.: Cambridge University Press; 2010.
[31] Kim et al., Anal Biochem. 1988; 174:168-76.
[32] Tierney et al., J Biomed Mater Res A. 2009; 91:92-101.
[33] Davidenko et al., Acta Biomater. 2010; 6:3957.
[34] Sethi et al., Wound Repair Regen. 2002; 10:397-408.
[35] Yannas et al., Philosophical Transactions of the Royal Society A: Math, Phys, Eng Sci. 2010; 368:2123-39.
[36] Chan & Yousaf, Mol Biosyst. 2008; 4:746-53.
[37] Petty et al., J Am Chem Soc. 2007; 129:8966-7.
[38] Dorman & Prestwich Biochemistry. 1994; 33:5661-73.
[39] Lee et al., J Biomed Mater Res A. 2007; 81:150-60.
[40] Hay et al., Mol Cell Biol. 2009; 29:953-64.
[41] Lu & Jiang, Adv Biochem Eng Biotechnol. 2006; 102:91-111.
[42] Murphy et al., Biomaterials. 2010; 31:461-6.
[43] Davidson, Chemical Communications. 1966(16):575.
[44] Turro, Modern Molecular Photochemistry. Mill Valley: University Science Books; 1991.
[45] Kang & Lipton. Photolabile and Miscellaneous Linkers/Resins. In: Tulla-Puche J, Albericio F, editors. The Power of Functional Resins in Organic Synthesis. Weinheim: Wiley-VCH; 2008. p. 467-492.
[46] Kuo &Tuan. Tissue Eng Part A 2008; 14(10):1615-27.
[47] Parikka et al., Matrix Biol 2005; 24(6):438-47.
[48] Gulotta et al., Am J Sports Med. 2010; 38:1429.
[49] Tierney et al. J Biomed Mater Res A 2009; 91:92-101.
[50] Riboh et al., J Hand Surg [Am] 2008; 33(8):1388-96.
[51] Klein et al., J Hand Surg [Am] 2002; 27(4):615-20.
[52] Caporali et al., TGF-b and microtopographical cues promote expression of tenogenic marker genes and tenocyte alignment. In: Proceedings of the 36th Annual Conference of the Veterinary Orthopedic Society; 2009; 2009.
[53] Ramery et al., Veterinary Immunology and Immunopathology 2009; 127(3-4):197-202.
[54] Genin et al., Biophysical Journal. 2009; 97(4):976-985.
[55] Monaco et al., Stem Cell Res Ther 2010; 1(1):7.
[56] Moffat et al., Tissue Eng Part A 2009; 15(1):115-126.
[57] Li et al., Annu Rev Biomed Eng. 2005; 7:105-50.
[58] Chawla et al., Tissue Eng Part C Methods 2010; 16:301-310.

We claim:

1. A method of immobilizing one or more types of biomolecules onto a collagen-glycosaminoglycan three-dimensional scaffold comprising:
   (a) adding benzophenone to a collagen-glycosaminoglycan three-dimensional scaffold in the dark;
   (b) adding one or more biomolecules to one or more areas of the collagen-glycosaminoglycan three-dimensional scaffold in the dark; and
   (c) exposing the collagen-glycosaminoglycan three-dimensional scaffold to light at a wavelength of about 350 to about 365 nm.

2. The method of claim 1, wherein one or more portions of the collagen-glycosaminoglycan three-dimensional scaffold are exposed to the light while one or more other portions of the scaffold remain in the dark.

3. The method of claim 2, wherein the one or more types of biomolecules are immobilized onto the scaffold at two or more different depths into the scaffold.

4. The method of claim 1, wherein two or more types of biomolecules are immobilized to the scaffold, and wherein the two or more types of biomolecules are immobilized to two or more areas of the scaffold, or to two or more depths in the scaffold, or both.

5. The method of claim 1, wherein a first mask is placed over the collagen-glycosaminoglycan three-dimensional scaffold prior to exposing the collagen-glycosaminoglycan three-dimensional scaffold to the light.

6. The method of claim 5, further comprising:
   (d) placing the collagen-glycosaminoglycan three-dimensional scaffold in the dark and removing the first mask from the collagen-glycosaminoglycan three-dimensional scaffold;
   (e) adding one or more biomolecules to one or more areas the collagen-glycosaminoglycan three-dimensional scaffold in the dark;
   (f) placing a second mask over the collagen-glycosaminoglycan three-dimensional scaffold in the dark;
   (g) exposing the collagen-glycosaminoglycan three-dimensional scaffold to light at a wavelength of about 350 to about 365 nm; and optionally repeating steps (d) to (g) with additional masks and biomolecules.

7. The method of claim 1, wherein the one or more of the biomolecules are immobilized to the scaffold via a cleavable linker.

8. The method of claim 7, wherein the cleavable linker is cleavable by an exogenous cue.

9. The method of claim 1, wherein the one or more biomolecules are peptides, proteins, carbohydrates, cytokines, hormones, nucleic acid molecules, integrins, antibodies, specific binding fragments of antibodies, or a biological sample.

10. The method of claim 7, wherein the cleavable linker is cleavable by an endogenous cue.

11. The method of claim 1, further comprising (d) seeding the collagen-glycosaminoglycan three-dimensional scaffold with cells.

* * * * *